United States Patent
Newell et al.

(10) Patent No.: US 7,271,883 B2
(45) Date of Patent: Sep. 18, 2007

(54) REFRACTIVE INDEX SENSOR USING INTERNALLY REFLECTIVE LIGHT BEAMS

(76) Inventors: Benjamin E. Newell, 1103 N. High Cross Rd., Urbana, IL (US) 61802; Ty A. Newell, 704 W. Michigan Ave., Urbana, IL (US) 61801

( * ) Notice: Subject to any disclaimer, the term of this patent is extended or adjusted under 35 U.S.C. 154(b) by 0 days.

(21) Appl. No.: 11/168,151

(22) Filed: Jun. 28, 2005

(65) Prior Publication Data
US 2006/0012776 A1    Jan. 19, 2006

Related U.S. Application Data

(60) Provisional application No. 60/587,525, filed on Jul. 13, 2004.

(51) Int. Cl.
*G01N 21/00* (2006.01)
(52) U.S. Cl. .................. 356/73; 356/436; 356/445
(58) Field of Classification Search ............... 356/133, 356/445, 73, 436
See application file for complete search history.

(56) References Cited

U.S. PATENT DOCUMENTS

| | | | |
|---|---|---|---|
| 5,694,210 A | 12/1997 | Newell et al. | |
| 2006/0068490 A1* | 3/2006 | Tang et al. | 435/287.2 |

* cited by examiner

*Primary Examiner*—Gregory J. Toatley, Jr.
*Assistant Examiner*—Kara Geisel
(74) *Attorney, Agent, or Firm*—Trexler, Bushnell, Giangiorgi, Blackstone & Marr, Ltd.

(57) ABSTRACT

A sensor system comprised of a diffuse light source and a sensor mounted on a transparent layer of material that is adjacent to a fluid. The refractive index of the transparent layer is greater than the refractive index of the fluid, causing a portion of the diffuse light source to be reflected from the interface of the transparent layer and the adjacent fluid. A sensor is placed at a location to intercept the reflected light. The diffuse light source and the sensor are optically coupled to the transparent layer with a transparent material wit a refractive index greater than that of the fluid. A light absorbing coating is placed ante surface of the transparent layer in order to absorb extraneous light from internal scattering of light from the fluid and light external to the sensor system.

15 Claims, 4 Drawing Sheets

REFRACTIVE INDEX SENSOR USING INTERNALLY REFLECTIVE LIGHT BEAMS

PRIORITY

This application claims the benefit of U.S. Provisional Application No. 60/587,525, filed on Jul. 13, 2004.

BACKGROUND OF THE INVENTION

1. Field of the Invention

In general, this invention relates to a sensor system for measuring the properties of a fluid. More specifically, this invention consists of a diffuse light source optically coupled to a transparent medium such that light rays beyond the critical angle at an interface between the transparent medium and a fluid are reflected back to a light sensor that is optically coupled to the transparent medium. Additionally, a light absorbing coating may be applied to the surface of the transparent medium to enhance the sensor's performance. The sensor allows the measurement of properties of the fluid such as refractive index and fluid mixture component concentration. An additional critical angle light "transmission" sensor may be incorporated for measuring light rays transmitted through the fluid that are less than the sensor system's critical ray angle. Light sensors for monitoring the "back scattering" of light, "forward scattering" of light, absorption of light, and transmission of light by the fluid medium may also be incorporated into the sensing system.

2. Description of Related Art

Real time measurement of fluid properties is important for the monitoring and control of processes. Refractive index is a property of a fluid that can be used to indicate the concentration or composition of a fluid that consists of multiple components. Some examples of processes in which fluid properties are of interest are refrigeration, food processing, juice dispensing, machining lubricants, battery and fuel cell electrolytes, and antifreeze mixtures.

Low cost, sensitive and reliable methods that can detect fluid mixture properties are desired. A variety of methods have been developed in order to determine a fluid's composition. Electrical conductivity can be used for fluids with electrolytic characteristics such as salt solutions. Polarimetry can be used for optically active fluids such as sugar-based fluids. Surface plasmon resonance can be used when a surface treated with a thin metallic coating, such as gold, can be directly exposed to the fluid. Coriolis force techniques and speed of sound techniques can be used when compositional changes result in fluid density changes. Viscosity methods can be used when the fluid's viscosity changes with compositional changes.

Refraction of light as it passes through a fluid is a method that can be utilized when variations of the fluid's composition or state affects the refractive index of the fluid. Some methods monitor the variation of a light beam's angle and/or displacement as it passes through the fluid. Other methods utilize the variation in the critical angle at an interface between the fluid and an adjacent material.

In addition to refractive index, determination of a fluid's light scattering and light absorption properties are also of interest. Methods that incorporate light scattering and light absorption measurement capabilities with refractive index measurement are desired. Dirt or other contaminants may increase the scattering and absorption characteristics of a fluid. Also, light scattering and absorption may indicate that an appropriate amount of additive, such as a pulp or fiber has been added to a system.

OBJECTS AND SUMMARY OF THE INVENTION

Accordingly, it is a general objective of the present invention to provide a sensor system for measuring properties of a fluid.

It is a more specific objective of the present invention to provide a sensor system for measuring the refractive index of a fluid.

It is another specific objective of the present invention to provide a sensor system which includes a diffuse light source and a reflected light sensor to intercept light rays beyond the critical angle at an interface between a transparent layer and a fluid.

It is another specific objective of the present invention to provide a sensor system including additional optical sensors to enhance the performance and reliability of the system.

It is another specific objective of the present invention to provide means for absorbing extraneous light in order to improve the performance and reliability of the system.

Summarily stated, the apparatus of the present invention comprises a sensor system for measuring the properties of a fluid including a diffuse light source, an optical sensor, and a transparent medium forming at least a portion of a fluid container, wherein the refractive index of the transparent medium is greater than the refractive index of a fluid contained in said fluid container so that a portion of the diffuse light source is reflected back from an interface between the transparent medium and the fluid to the sensor which is operatively associated with the transparent medium in order to intercept the reflected portion of the light source.

Preferably, the invention further includes a transparent bonding material for coupling the diffuse light source and the sensor to the transparent medium, the bonding material also having a refractive index greater than the refractive index of the fluid. Also, a light absorbing coating on the surface of the transparent medium, or the like, for enhancing the performance of the sensor system is included in the invention.

Ideally, the invention would include multiple optical sensors operatively associated with the transparent medium for measuring additional fluid properties.

A summary of the method of carrying out the present invention includes the steps of providing a fluid container including a transparent portion having a known refractive index, introducing a fluid into said container having a known refractive index which is less than the known refractive index of said transparent portion, operatively associating a diffuse light source and an optical sensor with said transparent portion of said fluid container, emitting diffuse light from said source into said transparent portion, and detecting light reflected back from an interface between the transparent portion of the fluid container and the fluid with the optical sensor.

BRIEF DESCRIPTION OF THE DRAWINGS

The features of the present invention which are believed to be novel are set forth with particularity in the appended claims. The organization and manner of operation of the invention, together with further objects and advantages thereof, may best be understood by reference to the following descriptions taken in connection with the accompanying drawings in which like reference numerals identify like elements, and in which:

DETAILED DESCRIPTION OF THE INVENTION

While the invention will be described in connection with a preferred embodiment, it will be understood that it is not intended to limit the invention to that embodiment. On the contrary, it is intended to cover all alternatives, modifications and equivalents as may be included within the scope and spirit of the invention.

This invention consists of a method and apparatus for measuring the refractive index variations and light scattering/absorption characteristics of a fluid by coupling a diffuse light source and light sensors to a transparent material adjacent to the fluid. The diffuse light source must be optically coupled to the transparent material such that light rays enter the material at an angle that will be greater than the critical angle between the transparent material and the adjacent fluid. Light rays that are incident on the fluid interface at angles greater than the critical angle are internally reflected within the transparent material. A light sensor is placed at a location to intercept the internally reflected light rays. The light sensor is optically coupled to the transparent wall material with a transparent bonding material that has a sufficiently high refractive index to allow the reflected light rays to be transmitted to the light sensor. A second light sensor may be placed on a second transparent layer opposing the first light transmitting layer in order to receive light transmitted through the fluid. The sensor would be placed in a region to measure light in a region where light ray angles are largely below the critical angle in order to add an additional means to detect refractive index variations of the fluid. In addition, light scattering and light absorption/transmission sensor elements that are less than and greater than the critical angle may be added to determine additional fluid properties related to the fluid.

Figure 1:
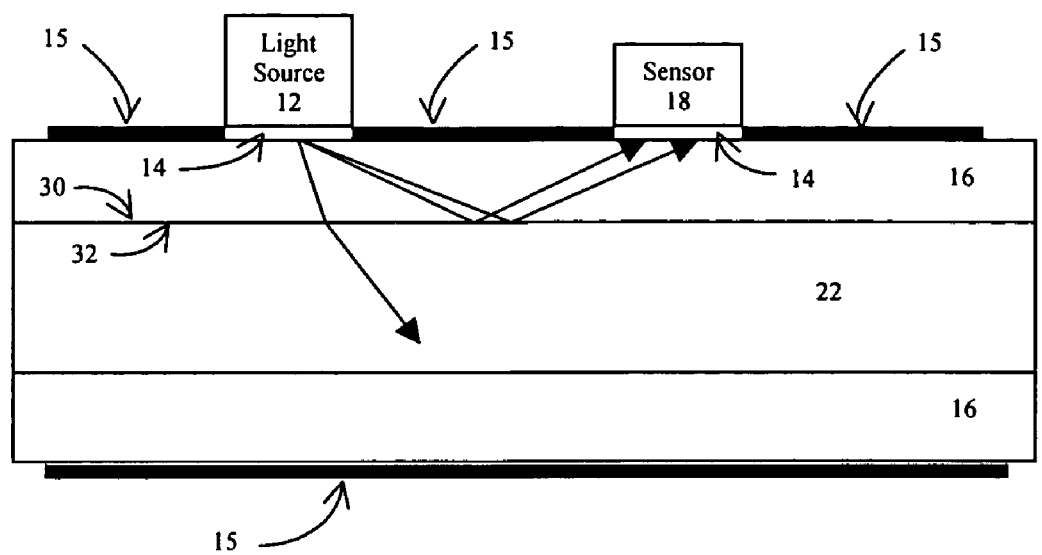
FIG. 1 is a side view of the sensor system of the present invention.

The diffuse light source (12) in FIG. 1 maybe a light emitting diode (LED). The LED may use light at different wavelengths (colors). The light passes through a transparent bonding material (14) to the transparent wall material (16). The transparent wall material may be glass or plastic with a refractive index greater than that of the fluid's (22) refractive index. As light rays reach the interface between the transparent wall (30) and the fluid (32), light rays less than the critical angle are partially transmitted into the fluid and partially reflected into the wall material. Light rays that are at angles greater than the critical angle are totally reflected back through the transparent wall material to the region where a light sensor (18) is located. The light sensor is coupled to the wall material with a transparent bonding material (14) with a sufficiently high refractive index to allow passage of the reflective light to the light sensor.

The light sensor (18) may be any sensor with sensitivity to the reflected light. Photoresistors, photodiodes, phototransistors are common sensors that may be utilized for light measurement. Also, light sensor arrays such as charge coupled devices (CCD) and linear diode arrays, may be bonded to the reflected light region in order to detect the location of light rays beyond the critical angle.

A light absorbing mask material (15) may be coated around the diffuse light source and light sensor in order to absorb extraneous light. Excess light from the diffuse light source may reflect off other surfaces and from scattering off particles in the fluid. Absorption of these light rays enhances the performance of the sensor and minimizes noise from the sensor system. The light absorbing mask may be a black paint, a dark plastic coating, or other material capable of absorbing extraneous light wavelengths or it may be part of an enclosure surrounding the sensor. The mask may also be coated over the transparent wall in a pattern where the light sensor is placed such that the amount of light on the sensor, and therefore the sensor's response is adjusted relative to the fluid's refractive index variation.

Figure 2:
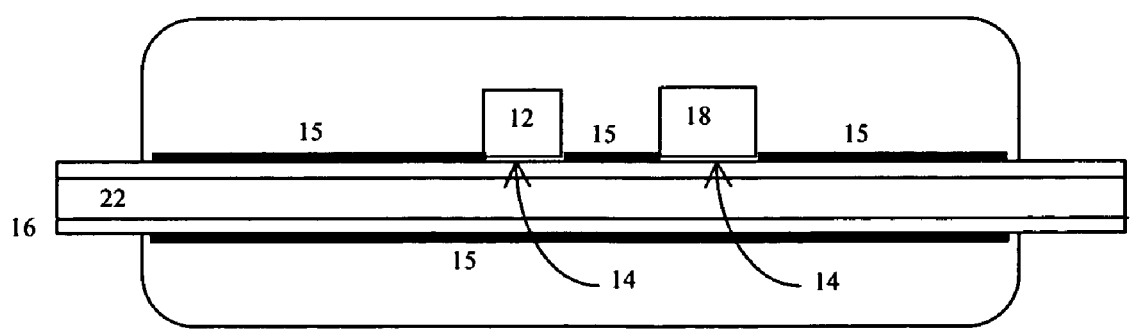
FIG. 2 is a side view of an alternative "flow through" embodiment of the present invention.

FIG. 2 shows an enclosed configuration of the sensor system where a transparent tube is used for passing a fluid through the sensor. Such a flow through sensor may be used for measurement of machine cutting fluid concentration, beverage dispensing sugar concentration, food processing monitoring, refrigerant concentration, and other similar process fluid monitoring. The sensor may be connected to an electronic display and/or connected to electronic monitoring circuits such as a microprocessor or digital signal processor.

Figure 3:
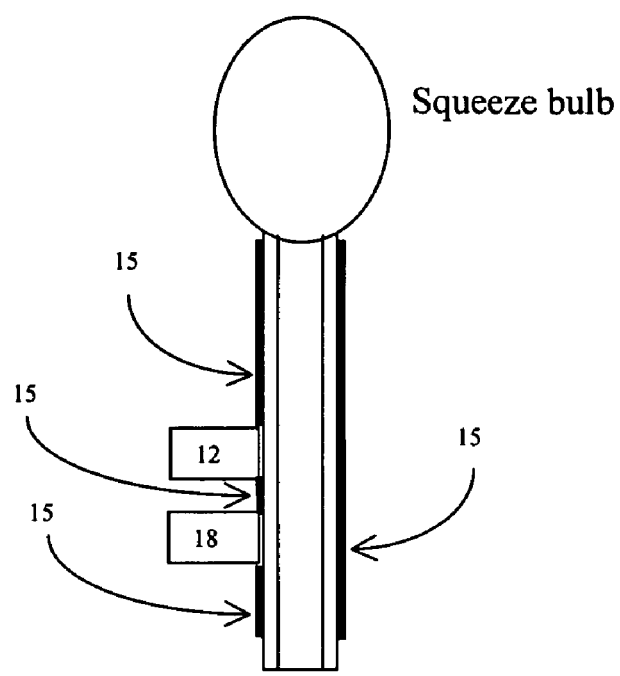
FIG. 3 is a side view of an another alternative embodiment of the present invention.

FIG. 3 shows an example of using the sensor for concentration or refractive index measurement of fluid samples that are drawn into a tube with a sensor mounted. Such a sensor configuration may be useful for extracting a fluid from a system. For example, monitoring the salinity of a salt water aquarium, measuring the charge of battery acid, or checking the concentration of an antifreeze solution may use a sensor of this type.

Figure 4:
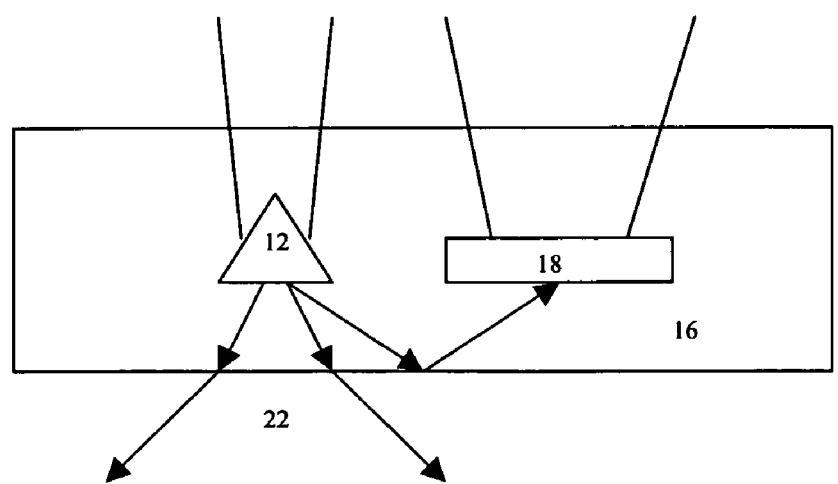
FIG. 4 is a side view of yet another alternative embodiment of the present invention.

FIG. 4 shows an "integrated" refractive index sensor in which the diffuse light source (12) and light sensor (18) are integrated into the transparent material (16) directly. Molding the light and light sensor components into a transparent plastic with proper spacing of the light source and light sensor will result in a compact sensor unit that may be used a refractive index "probe" or remote sensing head for making refractive index measurements in a fluid (22). The integrated sensor automatically couples the light source and light sensor optically to the transparent material, eliminating the need for an optically coupling bonding material.

Figure 5:
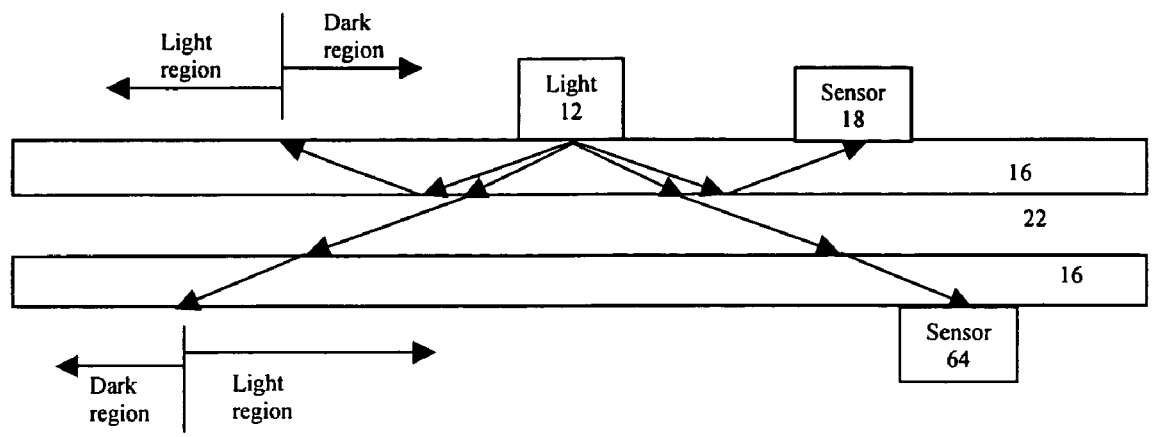
FIG. 5 shows a side view of still another alternative embodiment of the invention which incorporates a critical angle sensor.

FIG. 5 integrates a light transmission sensor (64) on an opposing transparent layer (16) that is located in a region where a strong light gradient occurs due to light rays near than the critical angle. Light rays less than the critical angle form a bright central region on the opposing transparent layer while light rays nearing the critical angle form a darkened region where light is not efficiently transmitted through the fluid (22). The light sensor (64) on the opposing transparent layer, in combination with the light sensor (18) on the initial transparent layer (16) may be used together to further improve the sensor system's sensitivity to refractive index and fluid concentration. It should be noted that the refractive index sensors work in opposing manners that further increases the sensitivity of the system. The light sensor (18) on the initial transparent layer with the light source (12) has decreased back reflected light as the fluid refractive index increases while the refractive index sensor (64) receiving transmitted light on the opposing transparent layer has increased light when the fluid refractive index increases.

Figures 6A, 6B:
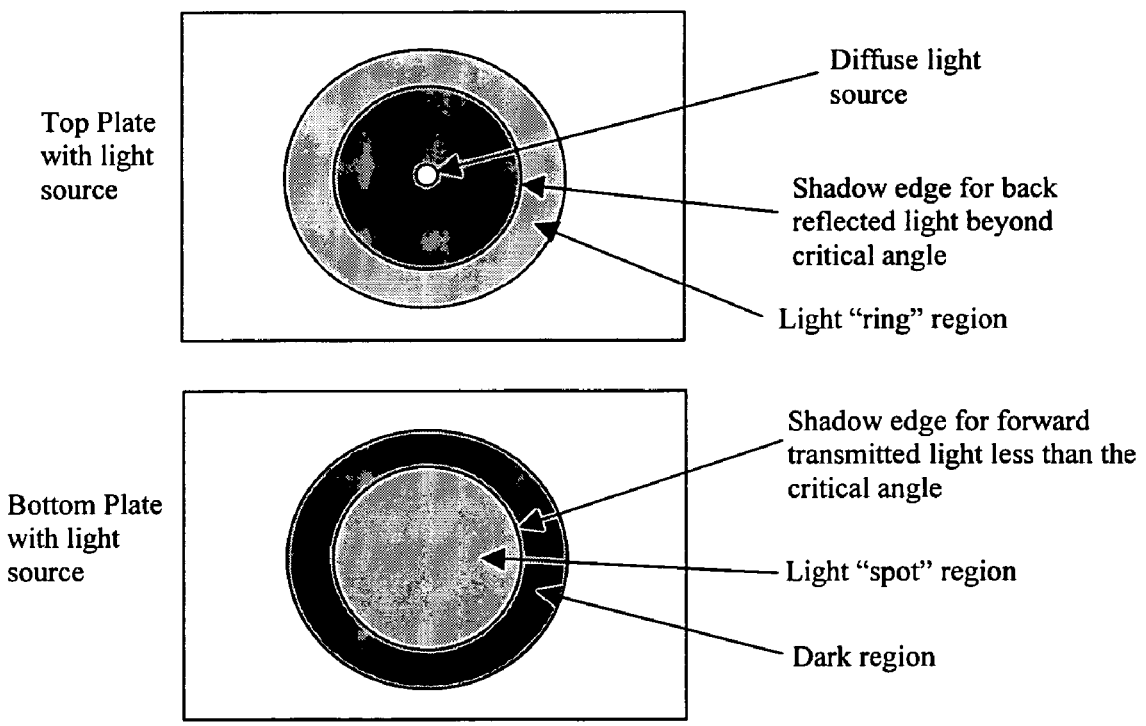
FIGS. 6a and 6b, respectively, are top and bottom views of the top and bottom surfaces in FIG. 5 showing the "shadow ring" region of the back reflected light on the top and the central light region of the transmitted light on the bottom.

FIG. 6a shows a plan view of the "top" transparent surface with the diffuse light source and back reflected light, and the opposing transparent layer receiving light less than the sensor system critical angle. The top layer has a "dark" region formed around the central spot where the diffuse light is placed on the transparent layer. A light region forms around the dark region on the top layer due to light greater than the critical angle between the top transparent layer and the fluid reflected back through the top transparent layer. The location of the boundary between the dark region and the bright region varies as the refractive index between the top transparent layer and the fluid varies.

FIG. 6b shows that the opposing transparent layer (bottom layer) has a central bright region surrounded by a dark region with a gradient of light that changes with changes in the refractive indices of the transparent layers relative to the fluid layer change. As the fluid's refractive index changes relative to the transparent layers, the size of the central bright region changes in size.

Figure 7:
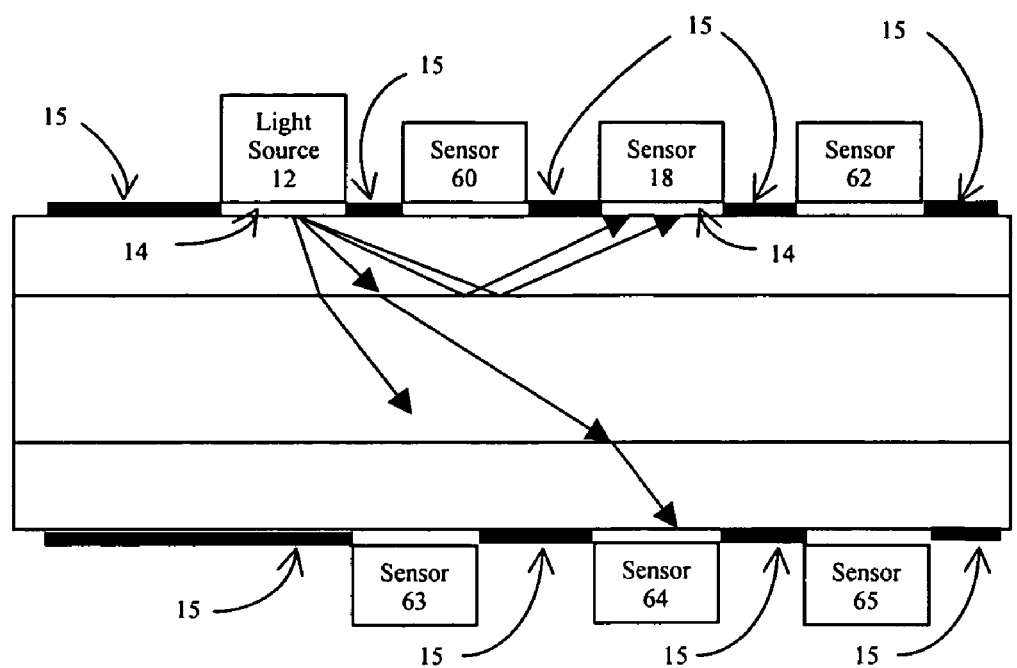
FIG. 7 is a side view of yet another alternative embodiment which incorporates additional optical sensors.
Figure 8:
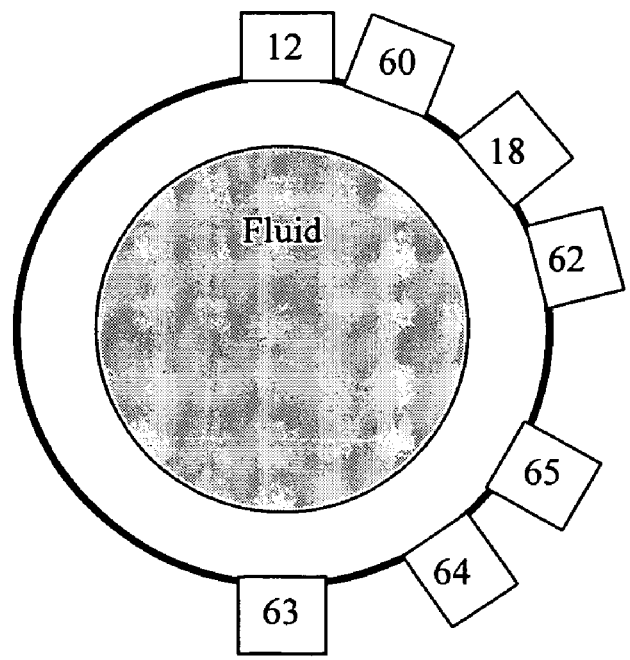
FIG. 8 is a side view of a final embodiment of the invention which implements a light source and sensors circumferentially around a circular tube.

FIG. 7 shows the inclusion of light scattering and light absorption/transmission sensors (60, 62, 63, 65) with top (18) and bottom (64) refractive index sensors in a light sensor system. Sensor 60 detects backscattered light that is less than the critical angle of the transparent layer (16) and the fluid (22). Sensor 62 detects light that is beyond the critical angle of the top transparent layer and the fluid. Light incident on sensor 62 may include light reflected at the interface between the top transparent layer and the fluid that is beyond the critical angle, and light that has been back reflected from the fluid due to scattering by particles in the fluid. Sensor 63 is placed on an opposing transparent layer and measures the amount of light transmitted through the fluid. Light in the bright region includes both directly transmitted light and forward scattered light from the light source. Sensor 65 is placed in the darker region of the opposing transparent layer, measuring the directly transmitted and forward scattered light from the light source. The sensors (18, 60, 62, 63, 64 and 65) in FIG. 7 may be used in varying combinations with each other in order to monitor changes in various fluid properties such as refractive index, particle concentration, fluid light absorption, fluid light transmission, back light scattering, forward light scattering and fluid clarity. The light scattering sensors (60, 62, 63, and 65) may either be optically coupled to the transparent layers using a sufficiently high refractive index bonding material, or the light scattering sensors may not be optically coupled to the transparent layer. It should be noted that light scattering sensor 62 for the measurement of backscattered light will not receive light internally reflected due to critical angle effects if an optical coupling is not implemented. When sensor 62 is optically coupled to the transparent layer, the sensor will receive both internally reflected light and back scattered light. FIG. 8 is similar to FIG. 7 and shows approximate locations of the light source and the light sensors when placed circumferentially on a circular tube.

While particular embodiments of the invention have been shown and described in detail above, it will be obvious to those skilled in the art that changes and modification of the present invention in its various aspects may be made without departing from the invention in its broader aspects, some of which changes and modifications being matters of routine engineering or design, and others being apparent only after study and analysis.

We claim:

1. A sensor system for measuring the properties of a fluid comprising:
    a single diffuse light source;
    multiple different types of optical sensors;
    a transparent medium forming at least a portion of a fluid container;
    wherein the refractive index of the transparent medium is greater than the refractive index of a fluid contained in said fluid container so that a portion of the diffuse light source is reflected back from an interface between the transparent medium and the fluid to said multiple different types of optical sensors which are operatively associated with the transparent medium in order to intercept the reflected portion of the light source.

2. A sensor system for measuring the properties of a fluid comprising:
    a single diffuse light source;
    multiple optical sensors;
    a transparent medium forming at least a portion of a fluid container;
    wherein the refractive index of the transparent medium is greater than the refractive index of a fluid contained in said fluid container so that a portion of the diffuse light source is reflected back from an interface between the transparent medium and the fluid to said multiple optical sensors which are operatively associated with the transparent medium in order to intercept the reflected portion of the light source, further comprising a light absorbing coating on the surface of the transparent medium for enhancing the performance of the sensor system.

3. A sensor system for measuring the properties of a fluid comprising:
    a single diffuse light source;
    multiple optical sensors;
    a transparent medium forming at least a portion of a fluid container;
    wherein the refractive index of the transparent medium is greater than the refractive index of a fluid contained in said fluid container so that a portion of the diffuse light source is reflected back from an interface between the transparent medium and the fluid to said multiple optical sensors which are operatively associated with the transparent medium in order to intercept the reflected portion of the light source, further comprising light absorbing enclosures surrounding the multiple optical sensors.

4. A sensor system for measuring the properties of a fluid comprising:
    a diffuse light source;
    an optical sensor;
    a transparent medium forming at least a portion of a fluid container;
    wherein the refractive index of the transparent medium is greater than the refractive index of a fluid contained in said fluid container so that a portion of the diffuse light source is reflected back from an interface between the transparent medium and the fluid to the sensor which is operatively associated with the transparent medium in order to intercept the reflected portion of the light source;
    and wherein multiple optical sensors are operatively associated with the transparent medium for measuring additional fluid properties and at least one of said multiple optical sensors measures the amount of light transmitted through the fluid.

5. A sensor system for measuring the properties of a fluid comprising:
   a diffuse light source;
   an optical sensor;
   a transparent medium forming at least a portion of a fluid container;
   wherein the refractive index of the transparent medium is greater than the refractive index of a fluid contained in said fluid container so that a portion of the diffuse light source is reflected back from an interface between the transparent medium and the fluid to the sensor which is operatively associated with the transparent medium in order to intercept the reflected portion of the light source;
   and wherein multiple optical sensors are operatively associated with the transparent medium for measuring additional fluid properties and at least one of said multiple optical sensors measures the amount of light absorbed by the fluid.

6. A sensor system for measuring the properties of a fluid comprising:
   a diffuse light source;
   an optical sensor;
   a transparent medium forming at least a portion of a fluid container;
   wherein the refractive index of the transparent medium is greater than the refractive index of a fluid contained in said fluid container so that a portion of the diffuse light source is reflected back from an interface between the transparent medium and the fluid to the sensor which is operatively associated with the transparent medium in order to intercept the reflected portion of the light source;
   and wherein multiple optical sensors are operatively associated with the transparent medium for measuring additional fluid properties and at least one of said multiple optical sensors measures the amount and direction of light scattered by the fluid.

7. A sensor system for measuring the properties of a fluid comprising:
   a single diffuse light source;
   multiple optical sensors;
   a transparent medium forming at least a portion of a fluid container;
   wherein the refractive index of the transparent medium is greater than the refractive index of a fluid contained in said fluid container so that a portion of the diffuse light source is reflected back from an interface between the transparent medium and the fluid to said multiple optical sensors which are operatively associated with the transparent medium in order to intercept the reflected portion of the light source, wherein said fluid container is constructed entirely from transparent material.

8. A method for determining one or more properties of a fluid comprising the following steps:
   providing a fluid container including a transparent portion having a known refractive index;
   introducing a fluid into said container having a known refractive index which is less than the known refractive index of said transparent portion;
   operatively associating a single diffuse light source and multiple different types of optical sensors with said transparent portion of said fluid container;
   emitting diffuse light from said source into said transparent portion;
   detecting light reflected back from an interface between the transparent portion of the fluid container and the fluid with said multiple different types of optical sensors.

9. A method for determining one or more properties of a fluid comprising the following steps:
   providing a fluid container including a transparent portion having a known refractive index;
   introducing a fluid into said container having a known refractive index which is less than the known refractive index of said transparent portion;
   operatively associating a single diffuse light source and multiple optical sensors with said transparent portion of said fluid container;
   emitting diffuse light from said source into said transparent portion;
   detecting light reflected back from an interface between the transparent portion of the fluid container and the fluid with said multiple optical sensors, further comprising the step of coating the transparent portion of the fluid container with a light absorbing material.

10. A method for determining one or more properties of a fluid comprising the following steps:
    providing a fluid container including a transparent portion having a known refractive index;
    introducing a fluid into said container having a known refractive index which is less than the known refractive index of said transparent portion;
    operatively associating a single diffuse light source and multiple optical sensors with said transparent portion of said fluid container;
    emitting diffuse light from said source into said transparent portion;
    detecting light reflected back from an interface between the transparent portion of the fluid container and the fluid with said multiple optical sensors, further comprising the step of providing light absorbing enclosures for said multiple optical sensors.

11. A method for determining one or more properties of a fluid comprising the following steps:
    providing a fluid container including a transparent portion having a known refractive index;
    introducing a fluid into said container having a known refractive index which is less than the known refractive index of said transparent portion;
    operatively associating a diffuse light source and an optical sensor with said transparent portion of said fluid container;
    emitting diffuse light from said source into said transparent portion;
    detecting light reflected back from an interface between the transparent portion of the fluid container and the fluid with the optical sensor;
    further comprising the step of providing multiple optical sensors for measuring additional fluid properties; and
    measuring the amount of light transmitted through the fluid.

12. A method for determining one or more properties of a fluid comprising the following steps:
    providing a fluid container including a transparent portion having a known refractive index;
    introducing a fluid into said container having a known refractive index which is less than the known refractive index of said transparent portion;

operatively associating a diffuse light source and an optical sensor with said transparent portion of said fluid container;

emitting diffuse light from said source into said transparent portion;

detecting light reflected back from an interface between the transparent portion of the fluid container and the fluid with the optical sensor;

further comprising the step of providing multiple optical sensors for measuring additional fluid properties; and measuring the amount the amount of light absorbed by the fluid.

13. A method for determining one or more properties of a fluid comprising the following steps:

providing a fluid container including a transparent portion having a known refractive index;

introducing a fluid into said container having a known refractive index which is less than the known refractive index of said transparent portion;

operatively associating a diffuse light source and an optical sensor with said transparent portion of said fluid container;

emitting diffuse light from said source into said transparent portion;

detecting light reflected back from an interface between the transparent portion of the fluid container and the fluid with the optical sensor;

further comprising the step of providing multiple optical sensors for measuring additional fluid properties; and measuring the amount and direction of light scattered by the fluid.

14. A method for determining one or more properties of a fluid comprising the following steps:

providing a fluid container including a transparent portion having a known refractive index;

introducing a fluid into said container having a known refractive index which is less than the known refractive index of said transparent portion;

operatively associating a single diffuse light source and multiple optical sensors with said transparent portion of said fluid container;

emitting diffuse light from said source into said transparent portion;

detecting light reflected back from an interface between the transparent portion of the fluid container and the fluid with said multiple optical sensors, further comprising the step providing an enlarged transparent portion of the fluid container such that two or more optical sensors can oppose one another.

15. A method for determining one or more properties of a fluid comprising the following steps:

providing a fluid container including a transparent portion having a known refractive index;

introducing a fluid into said container having a known refractive index which is less than the known refractive index of said transparent portion;

operatively associating a single diffuse light source and multiple optical sensors with said transparent portion of said fluid container;

emitting diffuse light from said source into said transparent portion;

detecting light reflected back from an interface between the transparent portion of the fluid container and the fluid with said multiple optical sensors, further comprising the step providing a fluid container which is constructed entirely of transparent material.

* * * * *